(12) United States Patent
Gagel

(10) Patent No.: US 9,656,012 B2
(45) Date of Patent: May 23, 2017

(54) METHOD AND DEVICE FOR DETERMINING AT LEAST ONE OPERATING PARAMETER OF A DEVICE FOR EXTRACORPOREAL BLOOD TREATMENT AS A FUNCTION OF ABSOLUTE PRESSURE; THE DEVICE FOR EXTRACORPOREAL BLOOD TREATMENT

(75) Inventor: Alfred Gagel, Litzendorf (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1176 days.

(21) Appl. No.: 13/493,341

(22) Filed: Jun. 11, 2012

(65) Prior Publication Data
US 2012/0316799 A1 Dec. 13, 2012

Related U.S. Application Data

(60) Provisional application No. 61/495,060, filed on Jun. 9, 2011.

(30) Foreign Application Priority Data

Jun. 9, 2011 (DE) .......................... 10 2011 106 111

(51) Int. Cl.
G01L 7/00 (2006.01)
G06F 19/00 (2011.01)
A61M 1/16 (2006.01)

(52) U.S. Cl.
CPC ........ *A61M 1/1686* (2013.01); *A61M 1/1601* (2014.02); *A61M 1/1658* (2013.01); *A61M 2205/3358* (2013.01)

(58) Field of Classification Search
CPC .... A61M 1/14; A61M 1/1601; A61M 1/1658; A61M 1/1686; A61M 2205/3358
(Continued)

(56) References Cited

U.S. PATENT DOCUMENTS 3,145,569 A 8/1964 Gilmont
4,086,653 A 4/1978 Gernes
(Continued)

FOREIGN PATENT DOCUMENTS

CN 101678161 3/2010
DE 199 19 572 11/2000
(Continued)

OTHER PUBLICATIONS

Weisstein, Least Squares Fitting, Sep. 2002.*
(Continued)

*Primary Examiner* — Michael Nghiem
*Assistant Examiner* — Peter Ngo
(74) *Attorney, Agent, or Firm* — Jacobson Holman, PLLC.

(57) ABSTRACT

A method and a device for determining an operating parameter of a device for extracorporeal blood treatment as a function of absolute pressure include setting the absolute ambient pressure in a closed container filled partially with air and having an essentially constant container volume by equalization of pressure with respect to the surroundings, and the pressure is maintained by isolating the container. With delivery means, a predetermined sequence of strokes of a liquid is delivered into or out of the container, and the change in the relative container pressure is measured after each delivery stroke. The total volume delivered and the relative pressure are assigned to a value pair, and the absolute pressure and the initial air volume is determined based on the Boyle-Mariotte law by using the value pairs for at least two delivery strokes. The operating parameter is calculated and adjusted as a function of the absolute pressure.

23 Claims, 2 Drawing Sheets

(58) Field of Classification Search
USPC .......................................................... 702/50
See application file for complete search history.

(56) References Cited

U.S. PATENT DOCUMENTS

| | | |
|---|---|---|
| 8,529,487 B2 | 9/2013 | Fava et al. |
| 2005/0171475 A1 | 8/2005 | Delnevo |
| 2006/0283450 A1 | 12/2006 | Shissler et al. |
| 2009/0099498 A1 | 4/2009 | Demers et al. |
| 2009/0124963 A1 | 5/2009 | Hogard et al. |
| 2010/0106071 A1* | 4/2010 | Wallenborg ........... A61M 1/166 604/5.01 |
| 2012/0083726 A1 | 4/2012 | Kopperschmidt et al. |
| 2012/0224987 A1* | 9/2012 | Jones ...................... F04B 17/04 417/420 |

FOREIGN PATENT DOCUMENTS

| | | |
|---|---|---|
| DE | 10 2009 024 864 | 12/2010 |
| GB | 592379 | 9/1947 |
| JP | 2003-11838 | 4/2003 |

OTHER PUBLICATIONS

George T. Verlag, "Technik der Hämadialyse und Antikoagulation"; 1973, 1997, Stuttgart, Germany, ISBN 3-13-497705-2, 10 pages total including translation.

Wikipedia—Pressure Meter, 4 pages total incl. translation; 13335490961939975018.

\* cited by examiner

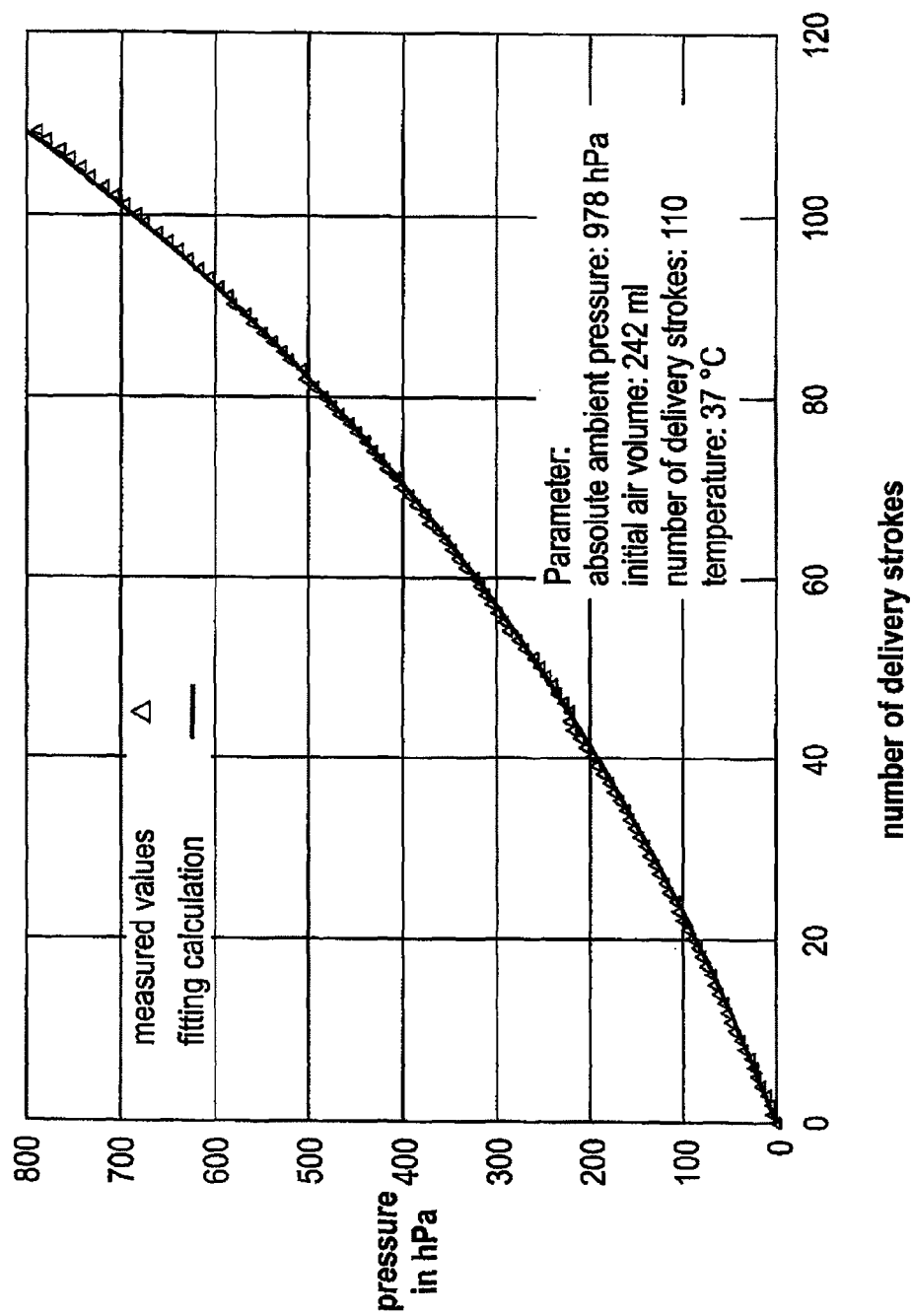

METHOD AND DEVICE FOR DETERMINING AT LEAST ONE OPERATING PARAMETER OF A DEVICE FOR EXTRACORPOREAL BLOOD TREATMENT AS A FUNCTION OF ABSOLUTE PRESSURE; THE DEVICE FOR EXTRACORPOREAL BLOOD TREATMENT

CROSS-REFERENCE TO RELATED APPLICATIONS

This application claims the benefit of U.S. provisional No. 61/495,060, and the priority of German number 10 2011 106 111.1, filed Jun. 9, 2011, hereby incorporated by reference.

BACKGROUND OF THE INVENTION

1. Field of Invention

The invention relates to a method and a device for determining at least operating parameter of a device for extracorporeal blood treatment as a function of the absolute pressure. For the sake of simplicity, the term blood treatment device is used hereinafter for all devices for extracorporeal treatment of blood.

2. Description of the Prior Art

Various types of blood treatment devices are known. The known blood treatment devices include, for example, devices for hemodialysis, hemofiltration and hemodiaflltration. During extracorporeal blood treatment, the blood flows through a blood treatment unit in an extracorporeal blood circulation. Of the devices for hemodialysis, hemofiltration and hemodiafiltration, the blood treatment unit is a dialyzer or filter which is separated by a semipermeable membrane into a blood chamber and a dialysis fluid chamber, when considered schematically. During the blood treatment by means of hemodialysis or hemodiafiltration, blood flows through the blood chamber while a dialysis fluid flows through the dialysis fluid chamber.

Fresh dialysis fluid may be supplied through a dialysis fluid system which is integrated into the device for extracorporeal blood treatment. Clean water, e.g., from reverse osmosis may be supplied to the dialysis fluid system after first being degassed and then mixed with liquid concentrates to prepare fresh dialysis fluid. Mixing may be accomplished, for example, by adding liquid concentrates to the clean water line at separate addition points and then mixing them thoroughly in a mixing chamber or by adding the liquid concentrates through separate feed points directly to a mixing chamber. The fresh dialysis fluid flows first through a balancing system and is then directed through the dialysis chamber of the dialyzer. The fresh dialysis fluid is then loaded with water and ingredients from the blood and thereby becomes spent dialysis fluid. After leaving the dialyzer, the spent dialysis fluid passes through the balancing system, where any difference between the volume of the fresh dialysis fluid and the spent dialysis fluid is determined.

The mixing chamber has incoming fluid lines and outgoing fluid lines. The mixing chamber may receive incompletely premixed mixture from degassed clean water and fluid concentrates. The complete mixing takes place in the mixing chamber. Fresh dialysis fluid is removed from the mixing chamber through a dialysis fluid line. Clean water, liquid concentrates and dialysis fluid are delivered in the lines by pumps. The clean water is degassed by creating a vacuum by means of a degassing pump in the clean water line upstream from the mixing chamber. The liquid concentrates are delivered by metering pumps upstream from the mixing chamber. The dialysis fluid is delivered through a dialysis fluid pump in the dialysis fluid line. With the dialysis fluid line upstream from dialyzer and with the dialysis fluid line downstream from the dialyzer, additional pumps may be in fluid connection, such as, for example, a flow pump in the dialysis fluid line and an ultrafiltration pump.

With the generic devices for extracorporeal blood treatment, inexpensive relative pressure sensors are usually used to measure the pressures. The pressures inside the dialysis fluid system are therefore usually set at ambient pressure. The generic devices for extracorporeal blood treatment therefore usually do not have an integrated absolute pressure gauge.

The operating parameters may be set as a function of the absolute pressure on known devices for extracorporeal blood treatment, which may be done either by a service technician using an external absolute pressure gauge or by storing approximate values in the central control unit.

The operating parameters are set by a service technician, who may carry an absolute pressure gauge with him for this purpose, as a function of the absolute pressure in setting up a blood treatment device in a selected geographic region, for example.

For example, according to the state of the art in setting up a blood treatment device, the elevation of the setup site is set through the choice of the value ranges and average values for the operating parameters which depend on the absolute pressure are preselected for each value range. For example, average values of the operating parameters depending on the absolute pressure are preselected for the following value ranges as a function of the elevation of the setup site above sea level:

setup height less than 800 meters above sea level (N.N.=normal zero of sea level),
setup height between 800 meters above sea level and 1400 meters above sea level,
setup height 1400 meters above sea level to 2000 meters above sea level,
setup height 2000 meters above sea level.

The elevation of the setup site can usually be estimated roughly without any additional assistance. The operating parameters predetermined for the value range are set according to the selection of a value range.

The known methods for setting operating parameters depending on the absolute pressure on blood treatment devices are associated with disadvantages because they are either complex and difficult to automate or they are inaccurate and also depend on the reliability of a user input that is susceptible to errors.

Examples of such operating parameters, which depend on the absolute pressure include the degassing pressure and the boiling point. The absolute pressure may also itself be an operating parameter of a device for extracorporeal treatment of blood.

The local ambient pressure may be between 700 hPa and 1060 hPa, for example, depending on the geographic location and the weather situation. An automatic adjustment in the operating parameters depending on the absolute pressure would also be desirable in the case of weather-related changes in the absolute pressure.

The degassing pressure must be set for a safe and reliable degassing of the clean water. The dissolving behavior of gases in liquids depends on the absolute pressure. The saturation concentration decreases with a decline in the absolute pressure. In generic blood treatment devices an absolute degassing pressure of approximately 150 hPa based on the vacuum is the goal. The degassing pressure is generated by a degassing pump and a throttle in the clean water line of the dialysis fluid system. Without an absolute pressure measurement, the degassing pressure can only be determined approximately. For a safe and reliable degassing, the most accurate possible setting of the degassing pressure is desirable.

The boiling point is needed to prevent steam from forming in hot cleaning of the dialysis fluid system because when steam forms it changes the flow properties in the dialysis fluid system and the steam can escape from the dialysis fluid system and enter the interior of the housing of the blood treatment device, where the steam can condense and lead to damage.

The boiling point drops with a drop in pressure. The change in the boiling point with the absolute pressure is known as a qualitative measure and can be obtained from the professional literature, for example, from tables for water and stored in the central control unit of the blood treatment device.

In heat disinfection of the dialysate system, the entire dialysis fluid system must be heated to more than 80° C. in a known device. The entire dialysis fluid system is especially advantageously purified by rinsing with hot water at approximately 85° C. In hot purification, the entire dialysis fluid system is rinsed with heated clean water at a predetermined flow rate. The clean water is heated with an electric heating rod. To keep the heating time of the clean water as short as possible, the clean water temperature on the heating rod should be as high as possible. The clean water temperature on the heating rod in the dialysis fluid system is always regulated at a temperature below the boiling point.

The absolute pressure may be appropriate for determining additional operating parameters. For example, in another patent application by the present applicant with the title "Method and Device for Testing the Delivery Power of at Least One Delivery Agent of a Device for Extracorporeal Blood Treatment": (internal application Ser. No. 10/57-d01 DE) with the same filing date as the present application, a method and a device for which knowledge of the absolute pressure is advantageous are described. Reference is thus herewith made to the full extent to the aforementioned other patent application.

For determining and providing many operating parameters, however, the existence of a current measured value of the absolute ambient pressure, also referred to simply as absolute pressure, would be advantageous. If there is a measured value for the absolute pressure, such operating parameters can be determined and adjusted with a particularly high precision.

SUMMARY OF THE INVENTION

One object of the invention is to further improve a generic blood treatment device without its own absolute pressure gauge such that at least one operating parameter which depends on the absolute pressure can be set automatically and without requiring an absolute pressure sensor or the use of a qualified service technician or a user.

Another object of the present invention is to determine at least one operating parameter depending on the absolute pressure with a high precision without requiring an absolute pressure gauge for this purpose.

Another object of the present invention is to automatically adjust at least one operating parameter, which depends on the absolute pressure when the absolute pressure in the surroundings changes significantly.

Another object of the present invention is to improve the user friendliness so that the user, for example, the treating physician or the dialysis nurse is not burdened with setting the operating parameters, which depend on the absolute pressure and therefore there are also no downtimes of the blood treatment machine for service by a qualified service technician.

Another object of the present invention is to increase the reliability of the blood treatment device. The more accurately the operating parameters which depend on the absolute pressure can be set, the more reliable the dialysis fluid system and thus the blood treatment device can operate reliably.

Another object of the present invention is to increase the safety of the blood treatment device. The more accurately the operating parameters which depend on the absolute pressure can be set, the more reliably the dialysis fluid system can operate.

These objects are achieved according to the invention with the features described herein. Advantageous embodiments of the invention are also described herein.

According to the teaching of the present invention, these objects are achieved by first setting the absolute ambient pressure in a closed container, which is filled at least partially with air and has an essentially constant container volume, and to do so through equalization of pressure with respect to the surroundings, and then this pressure is kept constant by cutting off the container from the surroundings and next a predetermined sequence of at least two delivery strokes of a fluid is delivered into the container using a delivery means and after each delivery stroke the increased relative pressure in the container is measured and after each delivery stroke the total volume delivered and the relative pressure are assigned to a value pair and the absolute pressure and/or the initial air volume is/are calculated using the value pairs for the at least two delivery strokes executed. The calculation may be performed on the basis of the Boyle-Mariotte law. According to the teaching of the invention these objects are additionally achieved by calculating the operating parameters which depend on the absolute pressure in an additional step.

The adjustment of the at least one operating parameter may in many embodiments include calculation and/or storage in a data memory in a control and computation unit. In many embodiments the adjustment of the at least one operating parameter may include execution of a control intervention on a function unit of the device for extracorporeal blood treatment. An example of a function unit is a pump with a controllable pump drive.

All the advantages that can be achieved with the method according to the invention can also be achieved in certain inventive embodiments in undiminished form with the device according to the invention and/or with the device for extracorporeal blood treatment. In some inventive embodiments this is also true of the inventive computer program product and the inventive computer program.

The method according to the invention may run automatically without requiring user intervention. The method according to the invention may be executed by a control and computation unit, which may be part of the device according to the invention. The method according to the invention may be started automatically by the control and computation unit at regular intervals, for example. A message that there is an automatic update of the operating parameters, which depend on the absolute pressure, may be displayed on the display screen of the blood treatment device while the method is being performed. During the update, the start of the blood treatment may be suppressed by the control and computation unit.

The control and computation unit may provide a means for limiting the relative pressure to a maximum level, so that unacceptably high pressures cannot occur. There may be an error message on the display of the blood treatment device indicating a failure of the update of the operating parameters which depend on the absolute pressure. On reaching an inadmissibly high relative pressure, the method according to the invention is terminated and may be restarted at a later point in time.

According to the teaching of the invention, these objects are further achieved by setting at least one calculated operating parameter on the blood treatment machine.

The absolute pressure is calculated merely on the basis of the measured values of the relative pressure in the closed container. The at least one operating parameter which depends on the absolute pressure may be calculated by the central control and computation unit of the blood treatment device and stored in a data memory and/or adjusted by control and/or regulating interventions. It is not necessary to use an absolute pressure gauge to do so.

The device according to the invention provides a closed container with an essential constant internal volume. An essentially constant container volume is understood to mean that the internal volume changes only negligibly or not at all with an increase in the internal pressure in the relevant pressure range. Closed is to be understood here to mean that there is no free opening with the surroundings while performing the method according to the invention and any inlet lines or outlet lines opening into the container but not needed for performing the method are cut off. Inlet lines or outlet lines may include, for example, tubing or pipelines. The inlet lines or outlet lines may be closed by valves. The inlet lines or outlet lines may be closed by pumps that are shut down. The inlet lines or outlet lines not needed for performing the method according to the invention are cut off by intervention measures by the control and computation unit before performing the method according to the invention.

In a preferred embodiment, the container is a mixing chamber in a dialysis fluid system of a blood treatment device for preparing fresh dialysis fluid.

The device according to the invention has means for measuring the relative pressure in the container. The means for measuring the relative pressure may be a pressure sensor in the container. In particular the means may be a pressure sensor in the air volume in the interior of the container but it may also be a pressure sensor which is functionally connected to the interior of the container for measuring the pressure. The pressure sensor provides an electrical pressure signal as a function of the relative pressure in the container, this signal being relayed over a data line to the control and computation unit. However, it is also possible for the pressure sensor to transmit the pressure signal wirelessly to the control and computation unit. The pressure sensor may be an RFID sensor. The means for measuring the relative pressure may be a relative pressure sensor which is present anyway in the mixing chamber of a dialysis fluid system.

The device according to the invention provides means for setting the absolute pressure (absolute ambient pressure) in the container. The absolute pressure level is initially unknown but is being sought. The means for initial setting of the absolute pressure may be a cutoff valve with which an opening in the otherwise closed container with respect to the surroundings can be opened or cut off for performing the additional steps of the method according to the invention.

The mixing chamber may have as an opening a line to the surroundings, the end of which is open to the surroundings. The line has a cutoff valve, with which the line can be closed in an airtight manner. The ambient pressure can be adjusted in the container easily by briefly opening the cutoff valve to the surroundings, so the pressure is equalized with the surroundings, and the absolute ambient pressure is automatically established in the container. After the pressure equalization, the cutoff valve is closed. The pressure thereby set remains upheld when the cutoff valve in the container is closed. The cutoff valve always remains closed to the surroundings during the following steps of the method according to the invention, so there cannot be a renewed equalization of pressure with respect to the surroundings. Only after the method according to the invention has been performed completely is a renewed pressure equalization with the surroundings ordered to depressurize the excess pressure that has been built up.

The valve may be automatically operable or operated. The valve can be opened and closed by the control and computation unit of the device according to the invention. However, the valve may also be operated by a manual control intervention by the user. For example, it may be a solenoid valve which is controllable electrically. However, it may also be a pneumatically controllable valve.

After setting the ambient pressure, an air volume which is referred to below as the initial air volume, is established in the container. The initial air volume fills the container at least partially. The remaining container volume may be filled with an initial liquid volume, which forms a liquid level. It is also possible for the complete internal volume of the container to be filled with air and to form the initial air volume. Then there is no liquid in the container.

Means for measuring the liquid volume may be present in the container. The means for measuring the liquid volume may be a filling level measurement by means of a filling level sensor. The filling level sensor delivers an electric filling level sensor as a function of the filling level in the container and this signal is forwarded over a data line to the control line computation unit. The liquid volume can be calculated by the control and computation unit from the measured filling level and the known geometry of the container. The initial air volume can be calculated as the difference between the container volume and the initial fluid volume. For performing the method according to the invention, means for measuring the liquid volume are not necessary because the initial air volume can be calculated by the method according to the invention but a filling level measurement may still be provided in the mixing chamber of a dialysis fluid system, so that it can advantageously be used for a plausibility check of the results of the calculation of the initial air volume. It is of course also possible to determine the initial air volume only by means of a filling level measurement.

It is also possible to analyze a measured filling level change as a criterion for a pressure change in the container by means of a filling level measurement in the container with known initial conditions of the pressure and air volume in the container as an alternative to the method according to the invention and from this to conclude the absolute pressure.

At least one liquid line having a fluid-carrying connection to a liquid source opens into the container; at least one delivery means for delivering the fluid in a first direction of delivery into the container is arranged in this liquid line. The delivery means is characterized in that there is no return flow through the delivery means in the opposite direction to the first direction of delivery when the delivery means is at a standstill. The delivery means functions like a non-return valve.

The delivery performance of the delivery means, in particular the delivery rate of the delivery means per delivery stroke and/or per unit of time is known and is stored in the control and computation unit. In a preferred embodiment, the delivery stroke may be a pump stroke. The liquid is incompressible or is assumed to be incompressible.

The at least one delivery means may be controlled by the control and computation unit for starting and stopping and/or for executing at least one delivery stroke. The at least one delivery means may be controlled by the control and computation unit for executing a sequence of delivery strokes. The delivery strokes may each have the same stroke volume but it is not necessary for the implementation of the invention for all the delivery strokes to have the same stroke volume. In a preferred embodiment, all the delivery strokes have the same stroke volume.

In a preferred embodiment, the liquid source is from the group of supplying clean water, supplying sodium bicarbonate concentrate and supplying acid concentrate from the dialysis liquid system of a blood treatment device.

In a preferred embodiment, the delivery stroke is the pump stroke of a diaphragm pump. The delivery behavior of a diaphragm pump is discontinuous from one delivery stroke to the next. The delivery volume of a complete pump stroke of a diaphragm pump depends only on the geometry of the diaphragm pump. With each complete pump stroke, the same volume of liquid can always be delivered.

Another preferred embodiment concerns the pump stroke of a piston pump. The delivery performance of a piston pump is discontinuous from one delivery stroke to the next. The pump stroke of a piston pump depends only on the geometry of the piston pump. The same volume of liquid can always be delivered with each complete pump stroke.

In another preferred embodiment, the pump stroke involves a predetermined delivery time of a delivery means having a continuous delivery performance. The delivery means may be, for example, a gear pump or a hose pump.

In a preferred embodiment, the delivery means may be a metering pump. The metering pump may be a high precision pump. The metering pump may be a diaphragm pump.

In an especially preferred embodiment, the pump stroke may be predefined by specifying a number of steps or a step angle on a stepping motor, which drives the delivery means. The stepping motor may be electrically operated. The step angle and/or the number of steps can be predetermined by electrical pulses of a control and computation unit.

The pressure in the container after adjusting the ambient pressure should change only through the supply of fluid through the pump strokes of the delivery means in the method according to the invention.

The delivery means can be controlled by a control and computation unit. The control and computation unit may be configured to induce a sequence of delivery strokes of the delivery means. The sequence of delivery strokes has a predetermined number of delivery strokes.

The control and computation unit may be configured to detect and/or save a measured pressure value in the container after each delivery stroke is completed.

The control and computation unit may additionally be configured to calculate the total liquid volume delivered after each delivery stroke is performed.

The total liquid volume delivered is understood to be the sum of the liquid volumes of all delivery strokes already performed while performing the method according to the invention.

In a preferred embodiment, the volume of each delivery stroke always has the same amount, namely a constant stroke volume. In this embodiment, the total liquid volume delivered is calculated especially easily as the product of the amount of the stroke volume and the number of delivery strokes performed.

The control and computation unit may additionally be configured to assign the amounts of the total liquid volume delivered and the relative pressure in the container to a value pair after each delivery stroke is made and to store them.

The control and computation unit may additionally be configured to automatically start the calculation of the absolute pressure and/or of the initial air volume on the basis of all value pairs as the next step after the conclusion and analysis of the last delivery stroke of a predetermined sequence of delivery strokes.

The control and computation unit may additionally be configured to calculate the absolute pressure and initial air volume parameters that are sought by way of a fitted calculation on the basis of all value pairs using the following approach, which is obtained by applying the Boyle-Mariotte law to the changes in state in the container such that a best possible approximation of the function described by this approach to the measured values of the relative pressure is obtained as follows:

$$P_i = P_{abs,amb} \cdot \frac{i \cdot V_{pump}}{V_{vessel,air,0} - i \cdot V_{pump}}; i = 1, \ldots, n$$

In equation (1), $P_{abs,amb}$ denotes the absolute pressure being sought in the surroundings, $V_{vessel,air,0}$ is the initial air volume being sought in the mixing chamber, $V_{pump}$ is the stroke volume of the diaphragm pump used here, n denotes the total number of delivery strokes of the diaphragm pump, i is the running index for the number of pump strokes and P is the relative pressure in the mixing chamber after performing a pump stroke.

The control and computation unit may additionally be configured to calculate the at least one operating parameter as a function of the absolute pressure.

The control and computation unit may additionally be configured to adjust the at least one calculated operating parameter in the blood treatment device as a function of the absolute pressure by means of control interventions. The at least one operating parameter can be adjusted through control intervention measures and/or regulating intervention measures on a control and computation unit.

The control and computation unit may additionally be configured to regulate the heating of clean water, which can be performed by means of an electric heater, so that the temperature of the clean water is always kept below a temperature limit which is below the boiling point. To this end, the control and computation unit can regulate the heating power and/or the on time of the electric heater. The electric heating may also be a heating rod.

The control and computation unit may additionally be configured to adjust the desired degassing pressure as a vacuum with respect to the absolute pressure by means of a control intervention on the degassing pump of the dialysis fluid system. The degassing pressure may be adjusted as a pressure drop on a degassing throttle in the clean water line by means of the rpm-regulated degassing pump. The degassing throttle may be a throttle valve, for example.

The device according to the invention may form an independent unit but may also be part of a blood treatment device. It may be a device for retrofitting a blood treatment device which does not have its own inventive container. An especially preferred embodiment provides that the device according to the invention is part of the blood treatment device because the known blood treatment devices already have components which can be utilized by the device according to the invention.

In another particularly preferred embodiment, equipping a blood treatment device with the device according to the invention may be limited to updating the software of the control and computation unit because all the required components are present in the blood treatment device through the software. For such embodiments and other embodiments, an inventive computer program with program code and an inventive computer program product with a program code stored on a machine-readable carrier are made available.

The device and the method according to the invention may be used with the known blood treatment devices without requiring any great renovation measures. A mixing chamber in a dialysis fluid system is present anyway with the known blood treatment devices. The means for measuring the relative pressure are present anyway on the known blood treatment devices. Retrofitting of a suitable chamber is possible without any great effort on blood treatment devices which do not have a mixing chamber in the dialysis fluid system. Suitable delivery means for delivering a fluid are always present in the dialysis fluid system of the known blood treatment devices.

BRIEF DESCRIPTION OF THE DRAWINGS

An exemplary embodiment of the invention is explained in greater detail below with reference to the figures. On the basis of the exemplary embodiment shown in the figures, additional details and advantages of the invention will be described in greater detail. The method and the device according to the invention are described on the example of a blood treatment device designed as a hemodialysis device. However, the method according to the invention may also be used in the same way with other blood treatment devices, for example, a hemodiafiltration device.

FIG. 2 shows a graphic plot of the pressure conditions of the relative pressure in the mixing chamber of the dialysis fluid system from FIG. 1 in performing the method according to the invention.

DETAILED DESCRIPTION OF THE PREFERRED EMBODIMENTS

Figure 1:
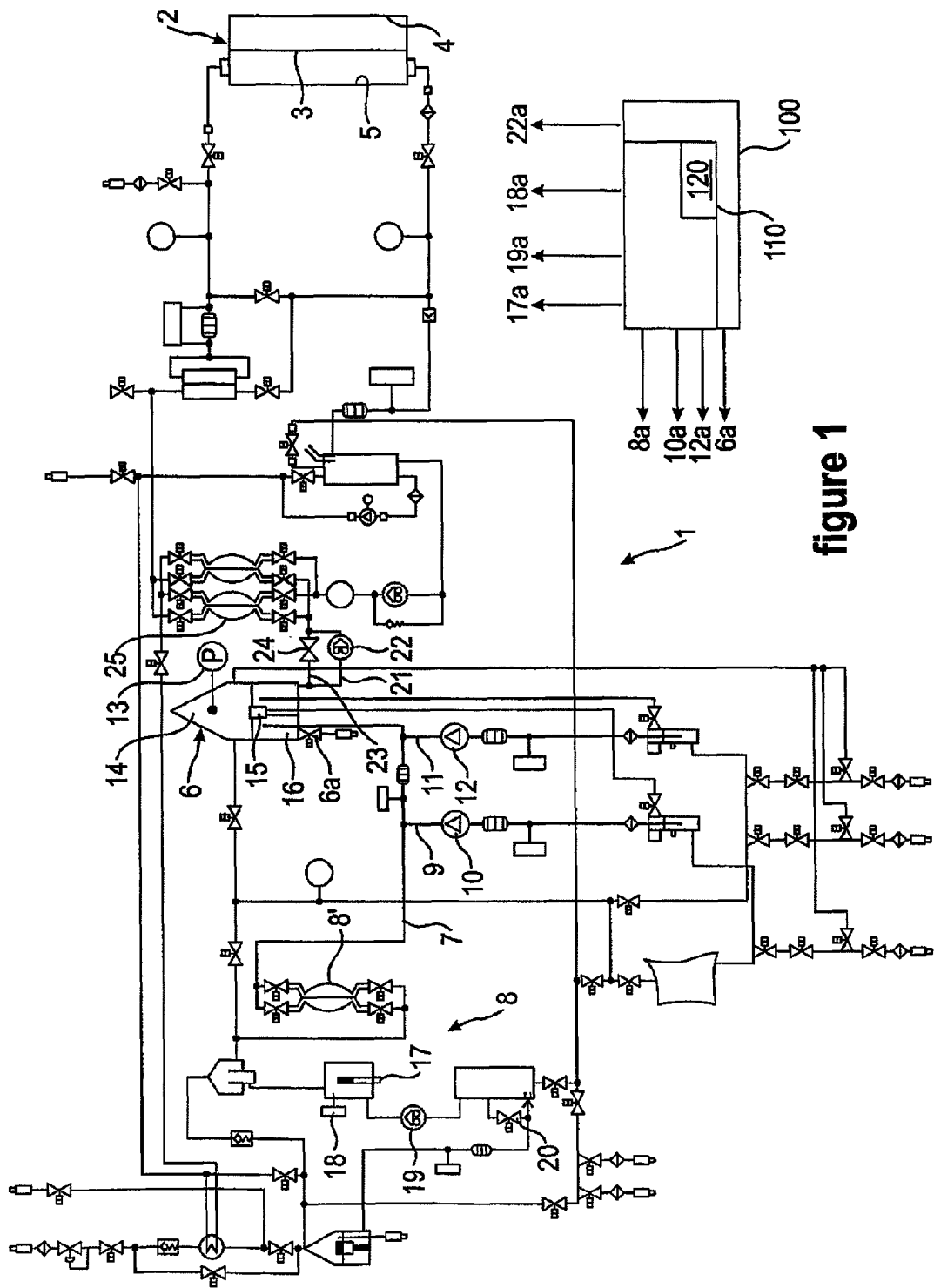
FIG. 1 shows a flow chart of the dialysis system of a blood treatment device having a mixing chamber, designed as a hemodialysis device.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

FIG. 1 shows in a simplified schematic diagram the essential components of the dialysis fluid system 1 of a blood treatment device designed as a hemodialysis device. In the present exemplary embodiment the blood treatment device which is designed as a hemodialysis device is referred to further in simplified terms as a "blood treatment device" having a dialyzer 2 which is separated schematically by a semipermeable membrane 3 into a blood chamber 4 and a dialysis fluid chamber 5. The blood chamber is part of the extracorporeal blood circulation (not shown) and the dialysis fluid chamber 5 is part of the dialysis fluid system 1. The central control and computation unit 100 operates and monitors the blood treatment device and the dialysis fluid system. The control and computation unit 110 of the device according to the invention is part of the central control and computation unit 100 of the blood treatment device in the exemplary embodiment. However, the control and computation unit 110 may also be separate from the central control and computation unit 100 and connected to the latter by data lines.

The dialysis fluid system has a mixing chamber 6 for mixing fresh dialysis fluid of clean water and liquid concentrates. The dialysis fluid system has a line 7 for delivering clean water to which a passive membrane 8' is connected, forming a delivery means having a metering function only in cooperation with a gear pump 19 (degassing pump), which is situated upstream and which is referred to hereinafter as delivery means 8. The line 7 opens into the mixing chamber 6. The delivery means 8 comprise delivery means for clean water.

A line 9 opens into the line 7 downstream from the delivery means for clean water 8. A delivery means 10 is connected to the line 9. The delivery means 10 in the exemplary embodiment is a metering pump for sodium bicarbonate concentrate. The metering pump 10 is embodied as a diaphragm pump.

Another line 11 also opens downstream from the delivery means for clean water 8 into the first line 7. Delivery means 12 is connected to the line 11. In this exemplary embodiment, the delivery means 11 is a metering pump for acid concentrate. The metering pump 12 is designed as a diaphragm pump.

A line 21 leads downstream from the mixing chamber 6 to the dialysis fluid chamber 5 of the dialyzer 2. One delivery means 22 is connected to line 21. In this exemplary embodiment, this delivery means is a gear pump 22, which is part of a balancing device 25. A bypass line 23 having a bypass valve 24 is provided in the parallel connection to the line 21. The bypass valve 21 is closed during operation of the gear pump 22.

In principle in the exemplary embodiment, each of the delivery means 8, 10, 12 or 22 may be selected for delivering a fluid into the container 6 or for delivering the fluid out of the container 6 for performing the method according to the invention. For delivering fluid into the container 6 the delivery means 8, 10 and 12 must be operated in the normal direction of delivery, while the delivery means 22 would have to be operated in the opposite direction of delivery. For delivering fluid out of the container 6, the delivery means 8, 10 and 12 would have to be operated in the reverse direction of delivery, while the delivery means 22 would have to be operated in the normal direction of delivery. In the present exemplary embodiment, the performance of the method according to the invention is explained as an example using the delivery means 10 with which fluid is delivered into the container 6 in the normal direction of delivery.

The control and computation unit 110 may have means for selecting one of the delivery means (8, 10, 12, and 22) for performing the method according to the invention. The choice may also be set fixedly in the control and computation unit 110 or may be made by the user through user intervention, for example, via the touchscreen of the blood treatment device (not shown in FIG. 1).

In the exemplary embodiment the diaphragm pump 10 for liquid concentrate is selected by the control and computation unit 110 as the delivery means. A delivery stroke of the diaphragm pump 10 in the present example corresponds exactly to the stroke volume which is delivered in the case of a complete pump stroke. This stroke volume of a complete pump stroke is known and constant for the selected pump. However, as an alternative the delivery stroke could also include part of a complete pump stroke, for example, if the pump drive is a stepping motor.

The control and computation unit 110 has means for ordering a predetermined number of delivery strokes. The delivery strokes are ordered by control intervention measures 10a.

The device according to the invention has a pressure sensor 13 which measures the relative pressure in the mixing chamber 6. The measured values of the pressure sensor 13 are transmitted to the control and computation unit 110 where they are stored in the data memory 120 for analysis.

In addition, the control and computation unit 110 has means for assigning the delivery volume delivered after each delivery stroke to the measured relative pressure in the mixing chamber as a value pair for the completed delivery stroke. The value pairs of all delivery strokes are stored in the control and computation unit 110.

In addition, the control and computation unit 110 has means for calculating the absolute ambient pressure and/or the initial air volume using the stored value pairs for all delivery strokes.

The calculations of the parameters that are sought are performed with the help of a computer program using program code to order the machine steps of the method and to analyze the measurement results. The computation equations are implemented in the program code. The program code is stored in the control and computation unit 110.

The computer program is stored as computer program product with the program code stored on a machine-readable carrier for ordering the machine steps of the method. The computer program runs in the control and computation unit 110. The control and computation unit 110 has a data memory 120.

The computer program with program code for ordering the machine steps of the method and for analyzing the measurement results starts the calculations as soon as the entire predetermined number of delivery strokes is concluded.

The total internal volume of the mixing chamber 6 is known and amounts to 350 mL in this exemplary embodiment. The initial liquid volume 16 in the mixing chamber 6 is calculated from the measured value of the filling level measurement device 15. The initial air volume 14 in the mixing chamber is calculated by the control and computation unit 110 as the difference in the total internal volume and the liquid volume and amounts to 242 mL in the exemplary embodiment. The temperature in the mixing chamber is 37° C. and is assumed to be constant while the method according to the invention is being performed.

The number of delivery strokes to be performed is advantageously more than 50 and especially advantageously up to 120. However, more than 120 delivery strokes are not necessary in the exemplary embodiment and do not yield a more accurate result. The number n of the delivery strokes to be performed is predefined as n=110, for example, in the central control of the blood treatment device in t his exemplary embodiment. The stroke volume of the diaphragm pump 10 in the exemplary embodiment is 1.0 mL (one milliliter) and corresponds to the delivery volume of a single delivery stroke in the diaphragm pump 10. The control and computation unit 110 starts and stops the delivery strokes of the diaphragm pump through control intervention measures 10a. With each delivery stroke one milliliter of liquid is pumped into the mixing chamber. There is no return flow of fluid through the diaphragm pump 10. The pressure in the mixing chamber increases with each delivery stroke in accordance with the Boyle-Mariotte law because with each delivery stroke the liquid volume increases by the amount of one delivery stroke, and on the other hand, the air volume decreases with each delivery stroke to the same extent by the amount of the delivery stroke. The air is therefore compressed by the same amount with each delivery stroke. This relationship is described by equation (1). The thermodynamic basis of equation (1) is the Boyle-Mariotte law applied to the changes in state of the air volume in the mixing chamber caused by the delivery strokes:

$$P_{abs,amb} \cdot V_{vessel,air,0} = (P_{abs,amb} + P_i) \cdot (V_{vessel,air,0} - i \cdot V_{pump}); i=1, \ldots, n \quad (1)$$

In equation (1), $P_{abs,amb}$ denotes the absolute ambient pressure being sought in the surroundings, $V_{vessel,air,0}$ denotes the initial air volume being sought in the mixing chamber, $V_{pump}$ denotes the stroke volume of the diaphragm pump, n denotes the total number of delivery strokes of the diaphragm pump, i denotes the running index for the number of pump strokes and $P_i$ denotes the relative pressure in the mixing chamber after the i-th pump stroke.

Equation (2) is obtained by rearranging equation (1) and is used in the program code for a fitting calculation to calculate the parameters $P_{abs,amb}$ and $V_{vessel,air,0}$ being sought, wherein no filling level sensor is needed:

$$P_i = P_{abs,amb} \cdot \frac{i \cdot V_{pump}}{V_{vessel,air,0} - i \cdot V_{pump}}; i = 1, \ldots, n \quad (2)$$

The calculation is performed under the assumption of a constant absolute pressure during the performance of the method according to the invention.

With the substitutions $x_i = i \cdot V_{pump}$ and $y_i = P_i$ the following equation is stored in the program code:

$$f(x_i) = P_{abs,amb} \cdot \frac{x_i}{V_{vessel,air,0} - x_i} \quad (3)$$

where n pump strokes are performed and n value pairs $(x_i, y_i)$, where i=1, . . . , n are determined. In these equations i=1, . . . , n denotes the running index for the sequence of pump strokes beginning with the first delivery stroke (i=1), the second delivery stroke (i=2) up to the last delivery stroke (i=n), so that a total of n delivery strokes are executed. The value pairs are stored in data memory 120.

Using the known fitting equation of "minimization of the sum of the distance squared," also known by the English term "method of least squares" applied to equation (2) together with equation (3), the parameters being sought are calculated on the basis of equation (4).

$$S = \sum_{i=1}^{n}(y_i - f(x_i))^2 = \sum_{i=1}^{n}\left(y_i - P_{abs,amb} \cdot \frac{x_i}{V_{vessel,air,0} - x_i}\right)^2 \quad (4)$$

The parameters $P_{abs,amb}$ and $V_{vessel,air,0}$ which are being sought are calculated according to the method of least squares so that the error total S in equation (4) assumes a minimum. The first of two necessary conditions for this is obtained from equation (5):

$$\frac{\partial S}{\partial P_{abs,amb}} = \frac{\partial}{\partial P_{abs,amb}} \sum_{i=1}^{n}\left(y_i - P_{abs,amb} \cdot \frac{x_i}{V_{vessel,air,0} - x_i}\right)^2 = \quad (5)$$

$$2 \cdot \sum_{i=1}^{n}\left(y_i - P_{abs,amb} \cdot \frac{x_i}{V_{vessel,air,0} - x_i}\right) \cdot \left(-\frac{x_i}{V_{vessel,air,0} - x_i}\right) = 0$$

It follows from equation (5) by rearranging:

$$\sum_{i=1}^{n}\left(y_i \cdot \frac{x_i}{V_{vessel,air,0} - x_i}\right) - P_{abs,amb} \cdot \sum_{i=1}^{n}\left(\frac{x_i}{V_{vessel,air,0} - x_i}\right)^2 = 0 \quad (6)$$

From equation (6) we obtain by rearranging a first determination equation for the two parameters being sought. The determination equation (7) is implemented in the program code.

$$P_{abs,amb} = \frac{\sum_{i=1}^{n}\left(y_i \cdot \frac{x_i}{V_{vessel,air,0} - x_i}\right)}{\sum_{i=1}^{n}\left(\frac{x_i}{V_{vessel,air,0} - x_i}\right)^2} \quad (7)$$

The first of two required terms is obtained according to equation (8):

$$\frac{\partial S}{\partial V_{vessel,air,0}} = \frac{\partial}{\partial V_{vessel,air,0}} \sum_{i=1}^{n}\left(y_i - P_{abs,amb} \cdot \frac{x_i}{V_{vessel,air,0} - x_i}\right)^2 = \quad (8)$$

$$2 \cdot \sum_{i=1}^{n}\left(y_i - P_{abs,amb} \cdot \frac{x_i}{V_{vessel,air,0} - x_i}\right) \cdot \left(+\frac{P_{abs,amb} \cdot x_i}{(V_{vessel,air,0} - x_i)^2}\right) = 0$$

Equation (8) yields a second determination equation (9) for the two parameters being sought.

$$\sum_{i=1}^{n}\left(y_i \cdot \frac{x_i}{(V_{vessel,air,0} - x_i)^2}\right) - P_{abs,amb} \cdot \sum_{i=1}^{n} \frac{x_i^2}{(V_{vessel,air,0} - x_i)^3} = 0 \quad (9)$$

Inserting the equation for the absolute pressure being sought according to equation (7) into equation (9) yields an implicit determination equation (10) for the parameter $V_{vessel,air,0}$ being sought. The determination equation (10) is implemented in the program code and is solved by a numerical problem-solving method in the known manner. The known numerical problem-solving method, selected, for example, from the bisection method (e.g., interval halving method) or regula falsi [the false position method] or the Newton-Raphson method is implemented in the program code.

$$\sum_{i=1}^{n}\left(\frac{y_i \cdot x_i}{(V_{vessel,air,0} - x_i)^2}\right) \cdot \sum_{i=1}^{n}\left(\frac{x_i}{V_{vessel,air,0} - x_i}\right)^2 - \quad (10)$$

$$\sum_{i=1}^{n}\left(\frac{y_i \cdot x_i}{V_{vessel,air,0} - x_i}\right) \cdot \sum_{i=1}^{n} \frac{x_i^2}{(V_{vessel,air,0} - x_i)^3} = 0$$

By inserting the calculated parameter $V_{vessel,air,0}$, equation (7) yields the second parameter $P_{abs,amb}$. It would of course also be possible to determine $P_{abs,amb}$ first and then $V_{vessel,air,0}$ in the opposite order.

The absolute pressure being sought is calculated as being 978 hPa in the exemplary embodiment and the initial air volume is calculated as 242 mL. It has surprisingly been found that the accuracy and reproducibility of the absolute pressure determined comply very well with the requirements of accuracy and reproducibility of the calculation of the operating parameters so that no direct measurement of the absolute pressure with an absolute pressure gauge is required.

FIG. 2 shows a graphic plot of the pressure conditions of the relative pressure in the mixing chamber of the dialysis fluid system from FIG. 1 in performing the method according to the invention. The number of 110 pump strokes performed is plotted on the abscissa. The relative pressure in the mixing chamber measured after each delivery stroke is plotted on the ordinate in FIG. 2 as a function of the number of pump strokes. The individual value pairs of the measured values of the relative pressure are represented by triangles in FIG. 2.

The absolute pressure parameter 978 hPa and the initial air volume 242 mL in the mixing chamber 6, which were calculated in performing the fitting calculation, are inserted into equation (2) yielding the fitted curve shown as a solid-line curve in FIG. 2. In other words the parameters of absolute pressure and initial air volume that are being sought are determined by the control and computation unit 110 by using the fitting equation and using all value pairs, so that the fitted curve according to equation (2) describes the dependence of the measured relative pressure on the number of delivery strokes in the best possible way. To avoid misunderstanding, it is pointed out that the absolute pressure cannot of course be read directly from the curve in FIG. 2.

The control and computation unit 110 calculates the at least one operating parameter, which depends on the absolute pressure after the absolute pressure has been determined in another step.

In the present exemplary embodiment the control and calculation unit 110 calculates the boiling point being sought on the basis of the data stored in the control and computation unit for the vapor pressure table for water or on the basis of an approximation equation stored in the control and computation unit. The clean water temperature on the heating rod in the dialysis fluid system is regulated in such a way that it is below the boiling point. The clean water temperature during heat disinfection is especially advantageously always regulated at approximately 1.2° C. below the boiling point. The control and computation unit 110 regulates the heating process of the clean water on the heating rod 17 through regulating intervention measures 17a in such a way that the temperature of the clean water measured by means of the temperature sensor 18 after passing through the heating rod 17 differs from the calculated boiling point by 1.2° C. and therefore a buildup of steam is reliably prevented. No user intervention is required for this. An absolute pressure gauge is not needed according to the invention. The temperature of the clean water is regulated with a very high precision. The safety and reliability of the dialysis fluid system are thereby improved.

To set the desired degassing pressure, the control and computation unit 110 causes regulating intervention measures 19a on the degassing pump 19 based on the measured value of the absolute pressure of 150 hPa, such that the degassing pressure required as an example is reached. The degassing pressure is therefore set as the pressure drop on the degassing throttle 20 by means of the rpm-regulated degassing pump 19. The pressure drop on the degassing throttle 20 is measured (pressure measurement points not shown in FIG. 1) and transmitted to the control and computation unit 110. The pressure difference between the calculated absolute pressure and the desired degassing pressure (i.e., 978 hPa minus 150 hPa) is calculated by the control and computation unit 110 and preselected as the setpoint value for the regulation. The pressure drop on the degassing throttle 20 is measured with two relative pressure sensors (not shown in FIG. 1) upstream and downstream from the degassing throttle 20 and compared with the setpoint value of the pressure difference. The rotational speed of the degassing pump 19 is regulated by the regulating intervention measures 19a so that the required pressure difference of 828 hPa at the degassing throttle 20 drops and the desired degassing pressure is reached. No user intervention measure is necessary for this. An absolute pressure gauge is not required according to the invention. The degassing pressure is set very accurately. The safety and reliability of the dialysis fluid system are thereby improved.

The control and computation unit 110 stores all the results in the memory 120. The memory content of the data memory 120 can be displayed on a display screen of the blood treatment device (not shown in FIG. 1) or can be read out of the memory via a data interface for documentation purposes.

The absolute pressure cannot be displayed visibly for the user, for example, the absolute pressure may be displayed as a numerical value on the display screen of the blood treatment device.

According to the invention the objects of the present invention are solved with the exemplary embodiment presented here. However, the present invention is not limited to this exemplary embodiment.

The invention being thus described, it will be apparent that the same may be varied in many ways. Such variations are not to be regarded as a departure from the spirit and scope of the invention, and all, such modifications as would be recognized by one skilled in the art are intended to be included within the scope of the following claims.

| List of reference numerals | |
|---|---|
| Reference numeral | Explanation |
| 1 | dialysis fluid system |
| 2 | dialyzer |
| 3 | semipermeable membrane |
| 4 | blood chamber |
| 5 | dialysis fluid chamber |
| 6 | mixing chamber |
| 7 | first line |

| List of reference numerals | |
|---|---|
| Reference numeral | Explanation |
| 8 | first delivery means, metering chamber/diaphragm pump |
| 8a | control intervention |
| 9 | second line |
| 10 | second delivery means, metering pump/diaphragm pump |
| 10a | control intervention |
| 11 | third line |
| 12 | third delivery means, metering pump/diaphragm pump |
| 12a | control intervention |
| 13 | pressure sensor |
| 14 | initial air volume |
| 15 | filling level measurement device |
| 16 | initial filling volume |
| 17 | heating rod |
| 17a | regulating measure |
| 18 | temperature sensor |
| 19 | degassing pump |
| 19a | control intervention |
| 20 | degassing throttle |
| 21 | Line |
| 22 | gear pump |
| 22a | control intervention |
| 23 | bypass line |
| 24 | cutoff valve |
| 25 | balancing device |
| 100 | central control and computation unit |
| 110 | control and computation unit |
| 120 | data memory |

What is claimed is:

1. A method of determining an operating parameter of a device for extracorporeal blood treatment as a function of absolute pressure, said method comprising the following steps:

setting ambient pressure in a closed container filled at least partially with an initial air volume or in a closed container filled at least partially with an initial air volume and at least partially with a liquid;

delivering a fluid to the closed container which is filled at least partially with the initial air volume by a sequence of at least two delivery strokes of a delivery device having predetermined stroke volumes, or delivering a fluid from the closed container filled at least partially with the initial air volume and at least partially with the liquid by a sequence of at least two delivery strokes of a delivery device with the predetermined stroke volumes;

calculating a total volume delivered after each delivery stroke;

measuring a relative pressure in the container after each delivery stroke;

assigning the total volume delivered after each completed delivery stroke and the measured volume of the relative pressure in the container after each completed delivery stroke to a value pair for the delivery stroke completed;

determining the absolute ambient pressure and determining the initial air volume in the container using the value pairs for the sequence of delivery strokes completed; and calculating the operating parameter as a function of the determined absolute ambient pressure, the absolute ambient pressure and the initial air volume in the container being calculated using an equation system based on the Boyle-Mariotte law for changes in state of the air volume in the container, the equation system providing that $$P_i = P_{abs,amb} \cdot \frac{i \cdot V_{pump}}{V_{vessel,air,0} - i * V_{pump}}$$

$$i = 1, \ldots, n$$

such that in the equation system:
$P_i$ denotes the relative pressure in the container after the i-th delivery stroke,
$P_{abs,amb}$ denotes the absolute pressure in the surroundings,
$V_{vessel,air,0}$ denotes the initial air volume in the container,
$V_{pump}$ denotes the stroke volume of the delivery device,
n denotes the total number of delivery strokes of the delivery device, and
i denotes a running index for the number of delivery strokes.

2. The method according to claim 1, wherein the at least two delivery strokes have a same stroke volume, and the total volume delivered is calculated after each delivery stroke as a product of a number of the delivery strokes completed and the stroke volume.

3. The method according to claim 1, wherein the operating parameter is at least one of a boiling point and a degassing pressure.

4. The method according to claim 1, further comprising a step of storing the calculated operating parameter in a control and computation unit.

5. The method according to claim 1, further comprising a step of providing the stroke volume of a delivery stroke as at least one variable selected from the group consisting of a size of a volume, a number of steps, a step angle of a stepping motor, and a delivery duration of the delivery device.

6. The method according to claim 1, wherein the absolute ambient pressure and the initial air volume in the container are calculated by applying a fitting equation to the equation system.

7. The method according to claim 6, wherein the fitting equation is associated with a least squares method.

8. A device for determining an operating parameter of a device for extracorporeal blood treatment as a function of absolute pressure, said device comprising:
a closed container filled at least partially with an initial air volume, or
a closed container filled at least partially with liquid and at least partially with an initial air volume;
a delivery device for delivering a plurality of delivery strokes of a liquid to the container or out of the container;
a device for measuring relative pressure in the container; and
a control and computation unit configured for
executing at least two delivery strokes of the delivery device,
measuring the relative pressure in the container after each delivery stroke,
analyzing the relative pressure in the container after each delivery stroke,
calculating a total volume delivered after each delivery stroke,
assigning the total volume delivered after each delivery stroke completed and the relative pressure in the container after each delivery stroke to a value pair for the delivery stroke completed,
determining the absolute ambient pressure and calculating the initial air volume in the container by using the value pairs for the at least two delivery stroked completed, and
calculating the operating parameter as a function of the determined absolute ambient pressure,
the control and computation unit being configured for calculating the absolute ambient pressure and the initial air volume in the container with an equation system using the Boyle-Mariotte law for the changes in state of the air volume in the container, the equation system providing that $$P_i = P_{abs,amb} \cdot \frac{i \cdot V_{pump}}{V_{vessel,air,0} - i * V_{pump}}$$

$$i = 1, \ldots, n$$

such that in the equation system:
$P_i$ denotes the relative pressure in the container after the i-th delivery stroke,
$P_{abs,amb}$ denotes the absolute pressure in the surroundings,
$V_{vessel,air,0}$ denotes the initial air volume in the container,
$V_{pump}$ denotes the stroke volume of the delivery device,
n denotes the total number of delivery strokes of the delivery device, and
i denotes a running index for the number of delivery strokes.

9. The device according to claim 8, wherein the delivery strokes have a same stroke volume.

10. The device according to claim 8, wherein the operating parameter is at least one of a boiling point and a degassing pressure.

11. The device according to claim 8, wherein the control and computation unit is configured for storing the calculated operating parameter in a control and computation unit of the device for extracorporeal blood treatment.

12. The device according to claim 8, wherein the control and computation unit is configured for specifying the stroke volume of a delivery stroke of the delivery device as at least one variable selected from the group consisting of an amount of a volume, a number of steps, a step angle of a stepping motor, and a delivery time of the delivery device.

13. The device according to claim 8, wherein the control and computation unit is configured for calculating the absolute ambient pressure and the initial air volume in the container by applying a fitting equation to the equation system.

14. The device according to claim 8, wherein the delivery device includes a pump.

15. The device according to claim 14, wherein the pump is selected from the group consisting of a diaphragm pump, a piston pump, a hose pump, and a gear pump.

16. A blood treatment device comprising a dialysis fluid system and a device according to claim 8.

17. The blood treatment device according to claim 16, wherein the blood treatment device is a hemodialysis device or a hemodiafiltration device.

18. The device according to claim 16, wherein the control and computation unit of the device for determining the operating parameter as a function of the absolute pressure is a part of a central control and computation unit of the blood treatment device.

19. The device according to claim 16, wherein the container is a mixing chamber of a dialysis fluid system of the blood treatment device.

20. The device according to claim 9, wherein the delivery device includes a metering pump.

21. The device according to claim 20, wherein the metering pump meters clean water or a liquid concentrate into the mixing chamber.

22. A non-transitory computer readable medium comprising computer instructions stored therein for enabling a computer processor to perform a method of determining an operating parameter of a device for extracorporeal blood treatment as function of absolute pressure, the method including
setting ambient pressure in a closed container filled at least partially with an initial air volume or in a closed container filled at least partially with an initial air volume and at least partially with a liquid,
delivering a fluid to the closed container which is filled at least partially with the initial air volume by a sequence of at least two delivery strokes of a delivery device having predetermined stroke volumes, or
delivering a fluid from the container filled at least partially with the initial air volume and at least partially with the liquid by a sequence of at least two delivery strokes of a delivery means with predetermined stroke volumes,
calculating a total volume delivered after each delivery stroke,
measuring a relative pressure in the container after each delivery stroke,
assigning the total volume delivered after each completed delivery stroke and the measured value of the relative pressure in the container after each completed delivery stroke to a value pair for the delivery stroke completed,
determining the absolute ambient pressure and determining the initial air volume in the container using the value pairs for the sequence of delivery strokes completed, and
calculating the operating parameter as a function of the determined absolute ambient pressure,
the absolute ambient pressure and the initial air volume in the container being calculated using an equation system based on the Boyle-Mariotte law for changes in state of the air volume in the container, the equation system providing that $$P_i = P_{abs,amb} \cdot \frac{i \cdot V_{pump}}{V_{vessel,air,0} - i * V_{pump}}$$

$$i = 1, \ldots, n$$

such that in the equation system:
$P_i$ denotes the relative pressure in the container after the i-th delivery stroke,
$P_{abs,amb}$ denotes the absolute pressure in the surroundings,
$V_{vessel,air,0}$ denotes the initial air volume in the container,
$V_{pump}$ denotes the stroke volume of the delivery device,
n denotes the total number of delivery strokes of the delivery device, and
i denotes a running index for the number of delivery strokes.

23. A non-transitory computer readable medium comprising computer instructions stored therein for enabling a computer processor to perform a method of determining an operating parameter of a device for extracorporeal blood treatment as a function of absolute pressure in a device that includes
a closed container filled at least partially with an initial air volume, or
a closed container filled at least partially with liquid and at least partially with an initial air volume,
a delivery device for delivering a plurality of delivery strokes of a liquid to the container or out of the container,
a device for measuring relative pressure in the container, and
a control and computation unit that includes the computer processor and that is configured for
executing at least two delivery strokes of the delivery device,
measuring the relative pressure in the container after each delivery stroke,
analyzing the relative pressure in the container after each delivery stroke,
calculating a total volume delivered after each delivery stroke,
assigning the total volume delivered after each delivery stroke completed and the relative pressure in the container after each delivery stroke to a value pair for the delivery stroke completed,
determining the absolute ambient pressure and calculating the initial air volume in the container by using the value pairs for the at least two delivery strokes completed, and
calculating the operating parameter as a function of the determined absolute ambient pressure,
the control and computation unit being configured for calculating the absolute ambient pressure and the initial air volume in the container with an equation system using the Boyle-Mariotte law for the changes in state of the air volume in the container, the equation system providing that $$P_i = P_{abs,amb} \cdot \frac{i \cdot V_{pump}}{V_{vessel,air,0} - i * V_{pump}}$$

$$i = 1, \ldots, n$$

such that in the equation system:
$P_i$ denotes the relative pressure in the container after the i-th delivery stroke,
$P_{abs,amb}$ denotes the absolute pressure in the surroundings,
$V_{vessel,air,0}$ denotes the initial air volume in the container,
$V_{pump}$ denotes the stroke volume of the delivery device,
n denotes the total number of delivery strokes of the delivery device, and
i denotes a running index for the number of delivery strokes.

* * * * *